(12) United States Patent
Wang et al.

(10) Patent No.: US 6,201,001 B1
(45) Date of Patent: Mar. 13, 2001

(54) IMIDAZOLE ANTIPROLIFERATIVE AGENTS

(75) Inventors: Le Wang, Mundelein; Qun Li, Libertyville; Hing L. Sham, Mundelein; Keith W. Woods, Libertyville, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/365,936

(22) Filed: Aug. 2, 1999

(51) Int. Cl.⁷ .................................................. A61K 31/415
(52) U.S. Cl. ...................... 514/396; 514/399; 514/400; 548/335.1; 548/335.5; 548/339.5; 548/340.1; 548/341.1; 548/342.5; 548/343.1; 548/343.5
(58) Field of Search ..................... 514/396, 399, 514/400; 548/335.1, 335.5, 339.5, 340.1, 341.1, 342.5, 343.1, 343.5

(56) References Cited

U.S. PATENT DOCUMENTS 5,296,609 * 3/1994 McCort et al. .................. 548/325.1

FOREIGN PATENT DOCUMENTS

2122395 * 9/1972 (FR) .................................. 548/335.1

1081673 3/1998 (JP) .

OTHER PUBLICATIONS

Ohsumi, et al., "Synthesis and Antitumor Activity of Cis–Restricted Combretastains: 5–Membered Heterocyclic Analogues," Bioorganic & Medicinal Chemistry Letters, 1998 (8), pp. 3153–3158.

* cited by examiner

Primary Examiner—Frederick Krass
(74) Attorney, Agent, or Firm—B. Gregory Donner; Gregory W. Steele

(57) ABSTRACT

Compounds of formula I

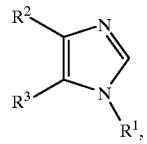

inhibit celluar proliferation. Processes for the preparation of the compounds, pharmaceutical compositions containing the compounds, and methods of treatment using the compounds are disclosed.

4 Claims, No Drawings

IMIDAZOLE ANTIPROLIFERATIVE AGENTS

TECHNICAL FIELD

The present invention relates to compounds useful for treating pathological states which arise from or are exacerbated by cell proliferation, to pharmaceutical compositions comprising these compounds, and to methods of inhibiting cell proliferation in a mammal.

BACKGROUND OF THE INVENTION

Neoplastic diseases, characterized by the proliferation of cells which are not subject to normal cell proliferating controls, are a major cause of death in humans and other mammals. Cancer chemotherapy has provided new and more effective drugs to treat these diseases and has also demonstrated that drugs which disrupt microtubule synthesis are effective in inhibiting the proliferation of neoplastic cells.

Microtubules play a key role in the regulation of cell architecture, metabolism, and division. The microtubule system of eucaryotic cells comprises a dynamic assembly and disassembly matrix in which heterodimers of tubulin polymerize to form microtubules in both normal and neoplastic cells. Within noeplastic cells, tubulin is polymerized into microtubules which form the mitotic spindle. The microtubules are then depolymerized when the mitotic spindle's use has been fulfilled. Agents which disrupt the polymerization or depolymerization of microtubules in neoplastic cells, thereby inhibiting the proliferation of these cells, comprise some of the most effective cancer chemotherapeutic agents in use.

Because of the pivotal role played by cell proliferation, agents which inhibit microtubule polymerization have been the subject of active current research for their clinical potential. See, for example, Bioorg. Med. Chem. Lett. 8 (1998) 3153–3158 and JP 10081673. But there is still a need for tubulin polymerization-inhibiting compounds with modified or improved profiles of activity.

SUMMARY OF THE INVENTION

In one embodiment of the present invention are disclosed tubulin polymerization-inhibiting compounds of formula I

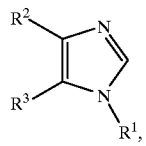

or a pharmaceutically acceptable salt or prodrug thereof, wherein $R^1$ is selected from the group consisting of hydrogen, methyl, ethyl, propyl, and iso-propyl; and one of $R^2$ or $R^3$ is 3,4,5-trimethoxyphenyl, and the other is phenyl substituted with one, two, or three substituents independently selected from the group consisting of alkoxy, halo, and $-NR^4R^5$, wherein $R^4$ and $R^5$ are independently selected from the group consisting of hydrogen and alkyl.

In another embodiment are disclosed compounds of formula I wherein $R^2$ is 3,4,5-trimethoxyphenyl.

In still another embodiment are disclosed compounds of formula I wherein $R^2$ is substituted phenyl.

In still yet another embodiment is disclosed a method of inhibiting tubulin polymerization in a mammal in recognized need of such treatment comprising administering to the mammal a therapeutically effective amount of of formula I.

In still yet another embodiment is disclosed a method of treating cancer in a mammal in recognized need of such treatment comprising administering to the mammal a therapeutically effective amount of of formula I.

In still yet another embodiment is disclosed a method of inhibiting tubulin polymerization in a mammal in recognized need of such treatment comprising administering to the mammal a therapeutically effective amount of of formula I wherein $R^2$ is 3,4,5-trimethoxyphenyl.

In still yet another embodiment is disclosed a method of treating cancer in a mammal in recognized need of such treatment comprising administering to the mammal a therapeutically effective amount of of formula I wherein $R^2$ is 3,4,5-trimethoxyphenyl.

In still yet another embodiment is disclosed a method of inhibiting tubulin polymerization in a mammal in recognized need of such treatment comprising administering to the mammal a therapeutically effective amount of formula I wherein $R^2$ is substituted phenyl.

In still yet another embodiment is disclosed a method of treating cancer in a mammal in recognized need of such treatment comprising administering to the mammal a therapeutically effective amount of formula I wherein $R^2$ is substituted phenyl.

In still yet another embodiment is disclosed a pharmaceutical composition which comprises a therapeutically effective amount of a compound of formula I in combination with a pharmaceutically acceptable carrier.

In still yet another embodiment is disclosed a a pharmaceutical composition which comprises a therapeutically effective amount of a compound of formula I, wherein $R^2$ is 3,4,5-trimethoxyphenyl, in combination with a pharmaceutically acceptable carrier.

In still yet another embodiment is disclosed a a pharmaceutical composition which comprises a therapeutically effective amount of a compound of formula I, wherein $R^2$ is substituted phenyl, in combination with a pharmaceutically acceptable carrier.

DETAILED DESCRIPTION OF THE INVENTION

Definition of Terms

The term "$C_1$–$C_3$ alcohol," as used herein, refers to methanol, ethanol, propanol, and iso-propanol.

The term "$C_1$–$C_4$ alkali metal alkoxide," as used herein, refers to lithium, sodium, or potassium methoxide, ethoxide, propoxide, iso-propoxide, 2-methylpropoxide, 1-methylpropoxide, and tert-butoxide.

The term "alkoxy," as used herein, refers to an alkyl group attached to the parent molecular group through an oxygen atom.

The term "alkyl," as used herein, refers to a monovalent group of one to six carbon atoms derived from a straight or branched chain saturated hydrocarbon.

The term "halo," as used herein, refers to —F, —Cl, —Br or —I.

The term "pharmaceutically acceptable salt," as used herein, refers to salts which are, within the scope of sound medical judgment, suitable for use in contact with the tissues of humans and lower animals without undue toxicity, irritation, or allergic response and are commensurate with a reasonable benefit/risk ratio. Pharmaceutically acceptable salts are well-known in the art. For example, S. M. Berge, et al. describe pharmaceutically acceptable salts in detail in J. Pharmaceutical Sciences, 1977, 66: 1 et seq, hereby incorporated by reference. The salts may be prepared in situ during the final isolation and purification of the compounds of the invention or separately by reacting a free base function with a suitable acid. Representative acid addition salts include acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl, and stearyl chlorides, bromides and iodides; and arylalkyl halides such as benzyl and phenethyl bromides. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, and ethylamine. Other representative organic amines useful for the formation of base addition salts include ethylenediamine, ethanolamine, diethanolamine, piperidine, and piperazine.

The term "pharmaceutically acceptable prodrugs," as used herein, refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to parent compounds of formula I, for example, by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are hereby incorporated by reference.

The present invention contemplates metabolites formed by in vivo biotransformation of compounds of formula I.

The term "metabolite," as used herein, refers to compounds formed by in vivo biotransformation of compounds of formula I by oxidation, reduction, hydrolysis, or conjugation. The present invention also contemplates compounds which undergo in vivo biotransformation such as by oxidation, reduction, hydrolysis, or conjugation to form compounds of formula I. A thorough discussion of biotransformation is provided in Goodman and Gilman's, *The Pharmacological Basis of Therapeutics*, seventh edition, hereby incorporated by reference.

Compounds falling within the scope of formula I include, but are not limited to, 2-methoxy-5-(1-methyl-4-(3,4,5-trimethoxyphenyl)-1H-imidazol-5-yl)phenylamine, 2-methoxy-5-(1-methyl-4-(3,4,5-trimethoxyphenyl)-1H-imidazol-5-yl)phenylamine, 5-(3-fluoro-4-methoxyphenyl)-1-methyl-4-(3,4,5-trimethoxyphenyl)-1H-imidazole, and N,N-dimethyl-4-(1-methyl-4-(3,4,5-trimethoxyphenyl)-1H-imidazol-5-yl)aniline.

DETERMINATION OF BIOLOGICAL ACTIVITY

Compounds of this invention were tested in a 48-hour cellular proliferation assay which uses human colon adenocarcinoma, MDR positive (HCT-15) cells, and human lung large cell carcinoma, MDR negative (NCI-H460) cells, in the 96-well microtitre format described in Skehan P., et al. New Colorimetric Cytotoxicity Assay for Anticancer Drug Screening. 1990, J. Natl. Cancer Inst. 82:1107–1112, hereby incorporated by reference. Briefly, the wells of a microtitre plate were charged sequentially with cultured cells and compounds of the invention ($1.0 \times 10^{-4}$ to $1.0 \times 10^{-11}$ M in 10% DMSO prepared by dissolving compounds of the invention in DMSO and adding 11 $\mu$L of the DMSO solution to 100 $\mu$L of culture medium for a final DMSO concentration of 10%). Two of the following controls were also present in each microtitre plate: a solvent (DMSO) control without drug that yielded a 0% inhibition level and a trichloroacetic acid-treated well that yielded a 100% inhibition level. The cells were grown in culture (37° C., 5% $CO_2$ atmosphere) for 48 hours then fixed by the addition of trichloroacetic acid. The wells were stained with sulforhodamine, washed with 1% acetic acid, and treated with 0.01M tris buffer (100 $\mu$L) to solubilize the adherent dye. The absorbance of the dye solution was measured with a Molecular Devices SpectraMax340 plate reader. The percent inhibition values were obtained by calculating the proportional response of the experimental values to the absorbance values of the controls. The results for compounds of formula I are shown in Table 1.

The pharmacokinetic behavior of selected compounds of formula I were evaluated in Sprague-Dawley rats, beagle dogs, and cynomolgus monkeys. In a series of parallel studies, groups of male rats (n=3/group), female cynomolgus monkeys (n=3/group), and beagle dogs (n=3/group) received a single 5 mg/kg IV or oral dose of selected compounds of formula I. The compounds were prepared as solutions in an ethanol:propylene glycol:D5W vehicle containing sodium hydroxide or hydrochloric acid (as needed for solubility) for both oral and IV dosing. All animals were fasted overnight prior to dosing and throughout the study. Water was provided freely. Sequential blood samples were obtained from each animal at selected time points after dosing. Plasma was separated by centrifugation at 4° C. and frozen until analysis. The parent drug was selectively removed from the plasma contaminants by liquid-liquid extraction with a mixture of ethyl acetate and hexanes under acidic conditions. The parent drug was separated from coextracted contaminants using reverse phase HPLC with MS quantitation of the analytes. The plasma concentrations of the representative compounds of formula I were plotted as plasma concentrations (ng/mL) versus time (hours after dosing) for both the IV and oral dosing, and areas under the curve (AUC's) were determined for each method of dosing. The data were normalized, and the fraction of drug available systemically (F) was determined for the representative compounds of formula I by dividing the AUC for the oral dosing by the AUC for the IV dosing.

The representative compounds of formula I tested showed a surprisingly high F values indicating excellent systemic blood levels.

TABLE 1

Inhibitory Potencies of Compounds of Formula I

| Example | $IC_{50}$ (nM) (HCT-15) | $IC_{50}$ (nM) (NCI-H460) |
| --- | --- | --- |
| 1 | 220 | 170 |
| 2 | 79 | 34 |
| 3 | 850 | 920 |
| 4 | 250 | 400 |

As shown by the data in Table 1 and the high F value determined from the pharmacokinetic studies, the compounds of the invention, including, but not limited to, those specified in the examples, are useful for the treatment of disease caused or exascerbated by cell proliferation. As cell proliferation inhibitors, these compounds are useful in the treatment of both primary and metastatic solid tumors and carcinomas of the breast, colon, rectum, lung, oropharynx, hypopharynx, esophagus, stomach, pancreas, liver, gallbladder, bile ducts, small intestine, urinary tract including kidney, bladder and urothelium, female genital tract including cervix, uterus, ovaries, choriocarcinoma, and gestational trophoblastic disease, male genital tract including prostate, seminal vesicles, testes, and germ cell tumors, endocrine glands including thyroid, adrenal, and pituitary, skin including hemangiomas, melanomas, sarcomas arising from bone or soft tissues including Kaposi's sarcoma, tumors of the brain, nerves, and eyes, meninges including astrocytomas, gliomas, glioblastomas, retinoblastomas, neuromas, neuroblastomas, Schwannomas and meningiomas, solid tumors arising from hematopoietic malignancies including leukemias and chloromas, plasmacytomas, plaques, tumors of mycosis fungoides, cutaneous T-cell lymphoma/leukemia, lymphomas including Hodgkin's and non-Hodgkin's lymphomas, prophylaxis of autoimmune diseases including rheumatoid, immune and degenerative arthritis, ocular diseases including diabetic retinopathy, retinopathy of prematurity, corneal graft rejection, retrolental fibroplasia, neovascular glaucoma, rubeosis, retinal neovascularization due to macular degeneration, hypoxia, abnormal neovascularization conditions of the eye, skin diseases including psoriasis, blood vessel diseases including hemagiomas and capillary proliferation within atherosclerotic plaques, Osler-Webber Syndrome, myocardial angiogenesis, plaque neovascularization, telangiectasia, hemophiliac joints, angiofibroma, and wound granulation.

The compounds of the present invention may also be useful for the prevention of metastases from the tumors described above either when used alone or in combination with radiotherapy and/or other chemotherapeutic treatments conventionally administered to patients for treating cancer. For example, when used in the treatment of solid tumors, compounds of the present invention may be administered with chemotherapeutic agents such as alpha inteferon, COMP (cyclophosphamide, vincristine, methotrexate, and prednisone), etoposide, mBACOD (methortrexate, bleomycin, doxorubicin, cyclophosphamide, vincristine, and dexamethasone), PRO-MACE/MOPP (prednisone, methotrexate (w/leucovin rescue), doxorubicin, cyclophosphamide, paclitaxel, etoposide/mechlorethamine, vincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like. Other chemotherapeutic agents include alkylating agents such as nitrogen mustards (mechloethamine, melphan, chlorambucil, cyclophosphamide and ifosfamide), nitrosoureas including carmustine, lomustine, semustine and streptozocin, alkyl sulfonates including busulfan, triazines including dacarbazine, ethyenimines including thiotepa and hexamethylmelamine, folic acid analogs including methotrexate, pyrimidine analogues including 5-fluorouracil and cytosine arabinoside, purine analogs including 6-mercaptopurine and 6-thioguanine, antitumor antibiotics including actinomycin D, anthracyclines including doxorubicin, bleomycin, mitomycin C and methramycin, hormones and hormone antagonists including tamoxifen, cortiosteroids and miscellaneous agents including cisplatin and brequinar. For example, a tumor may be treated conventionally with surgery, radiation, or chemotherapy, and compounds of formula I, then treated with additional compound of formula I to extend the dormancy of micrometastases and to stabilize and inhibit the growth of any residual primary tumor.

METHODS OF TREATMENT

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The term "parenteral," as used herein, refers to modes of administration which include intravenous, intramuscular, intraperitoneal, intrasternal, subcutaneous and intraarticular injection and infusion.

The pharmaceutical compositions of this invention can also be administered to humans and other animals orally, rectally, parenterally , intracisternally, intravaginally, intraperitoneally, topically (as by powders, ointments, or drops), bucally, or as an oral or nasal spray.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols such as glycerol, propylene glycol, polyethylene glycol, D5W (5% dextrose in water), and the like, and suitable mixtures thereof, vegetable oils such as olive oil, and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents such as paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin. In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention. Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

SYNTHETIC METHODS

The compounds and processes of the present invention will be better understood in connection with the following synthetic schemes, which illustrate methods by which the compounds of the invention may be prepared. The compounds of formula I can be prepared by a variety of synthetic routes. Representative procedures are shown in Scheme 1. The groups $R^1$, $R^2$, and $R^3$ are previously defined, and LG is defined in the description of Scheme 1.

It will still further be apparent to one of ordinary skill in the art that $R^1$, $R^2$, and $R^3$ can be determined by selection of the appropriate commercially available or known starting materials or introduced synthetically by known chemical methods such as those disclosed in Larock, "Comprehensive Organic Transformations. A Guide to Functional Group Preparations," VCH Publishers, New York (1989), hereby incorporated by reference.

It will further be apparent to one skilled in the art that the selective protection and deprotection steps, as well as order of the steps themselves, can be carried out in varying order, depending on the nature of groups $R^1$, $R^2$, and $R^3$ to successfully complete the syntheses of compounds of formula I. Commonly used protecting groups are disclosed in Greene, "Protective Groups In Organic Synthesis," John Wiley —Sons, New York (1981), hereby incorporated by reference.

ABBREVIATIONS

Abbreviations used in the descriptions of the schemes and the examples are: THF for tetrahydrofuran; DME for 1,2-dimethoxyerhane; and TMBE for tert-butyl methylether; DMSO for dimethylsulfoxide; DCM for dichloromethane.

Scheme 1

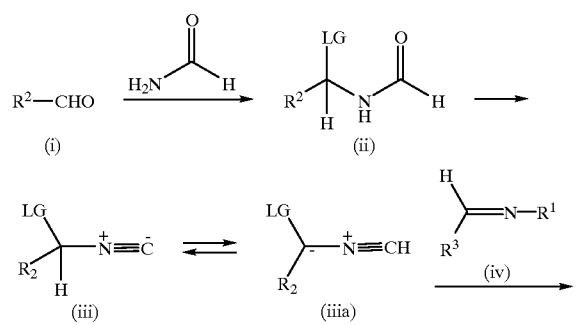

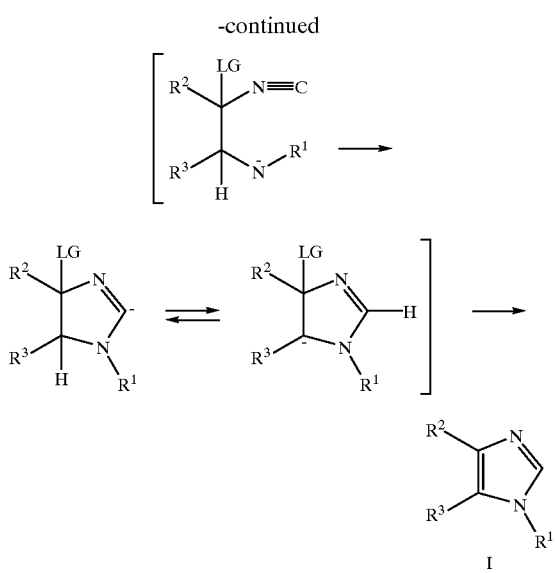

As shown in Scheme 1, compounds of formula I can be prepared by acid catalyzed treatment of the appropriately substituted benzaldehyde (i) with formamide and an optionally substituted benzenesulfinic acid to provide N-formylated (ii), wherein leaving group LG is optionally substituted benzenesulfonyl. For example, compounds of formula I, wherein $R^2$ is 3,4,5-trimethoxyphenyl, can be prepared from 3,4,5-trimethoxybenzaldehyde; and compounds of formula I, wherein $R^2$ is substituted phenyl, can be prepared from the corresponding substituted benzaldehyde. Although the solvent used in the reaction is not particularly limited, a solvent in which the starting materials are both soluble is generally used. Examples of such solvents include THF, dioxane, benzene, toluene, diethyl ether, chloroform, dichloromethane, DME, DMSO, or mixtures thereof. In a preferred embodiment, formamide itself is used as the solvent with any of the aformentioned solvents optionally present to facilitate dissolution of the other starting materials, as necessary. Since acid catalyzes the introduction of formamide to (i) but can also hydrolyze the formamide, it is preferable to run the reaction in the presence of an acid catalyst which will minimally hydrolyze the formamide. Examples of such acids include organic sulfonic acids such as optionally substituted benzene sulfonic acid, methane sulfonic acid, and camphorsulfonic acid. The reaction generally proceeds at elevated temperature, but the temperature can be raised or lowered, as needed. The reaction time is generally 30 minutes to 24 hours, depending on the types of starting materials and the reaction temperature.

Conversion of (ii) to isonitrile (iii) and its proton tautomer aminium (iiia) can be accomplished with a dehydrating agent such as $POCl_3$, $Cl_3C(O)C(O)Cl$, or an optionally substituted triaryl or trialkyl phosphine and carbon tetrachlorde. Although the solvent used in the reaction is not particularly limited, a solvent which is not reactive with the starting materials and in which the starting materials are both soluble is generally used. Examples of such solvents include THF, dioxane, benzene, toluene, diethyl ether, chloroform, DME, dichloromethane, or mixtures thereof. Since acid is liberated with the progress of the reaction, it is preferable to run the reaction in the presence of a suitable deacidifying agent. For this reason, the use of a basic solvent such as diisopropylethylamine, pyridine or triethylamine can be used, although the reaction can be run in any of the aformentioned solvents with at least a stoichiometric amount of base present. The reaction generally proceeds at room temperature, but it is preferably run at lower temperatures. The reaction time is generally 30 minutes to 18 hours and can be selected depending on the types of starting materials and the reaction temperature.

Imine (iv) can be prepared by treatment of an appropriately substituted benzaldehyde with a primary amine in the presence of an acid. Examples of acids include inorganic acids such as HCl, HBr, and $H_2SO_4$, and organic acids such as formic acid and acetic acid. Although the solvent used in the reaction is not particularly limited, a solvent which is not reactive with the starting materials and in which the starting materials are both soluble is generally used. Examples of such solvents include $C_1$–$C_3$ alcohols, THF, dioxane, benzene, toluene, DCM, chloroform, or mixtures thereof. Since water is liberated with the progress of the reaction, it can be useful to run the reaction in the presence of a solvent which forms a minimum boiling azeotrope with water, or to run the reaction in the presence of a drying agent such as $MgSO_4$, $Na_2SO_4$, or molecular sieves. The reaction generally proceeds at room temperature, but it can be run at lower or higher temperatures, as necessary. The reaction time is generally 30 minutes to 18 hours and can be selected depending on the types of starting materials, the solvent, whether or not a drying agent is present, and the reaction temperature.

The conversion of (iii)/(iiia) to compounds of formula I can be accomplished by treatment of the former with (iv) in the presence of base. Although the solvent used in the reaction is not particularly limited, a solvent which is not reactive with the starting materials and in which the starting materials are both soluble is generally used. Examples of such solvents include $C_1$–$C_3$ alcohols, THF, dioxane, benzene, toluene, DCM, chloroform, DME, or mixtures thereof. Examples of bases which can be used include alkali metal alkoxide bases such as $C_1$–$C_4$ alkali metal alkoxide bases, $Na_2CO_3$, $NaHCO_3$, $K_2CO_3$, and $KHCO_3$. The reaction involving addition of the imine to the tautomer, cyclization, and aromitization with accompanying explusion of leaving group LG generally proceeds at elevated temperature, but it can be run run at lower temperatures, as necessary. The reaction time is generally about 30 minutes to about 18 hours and can be selected depending on the types of starting materials and the reaction temperature. In a preferred embodiment, a solution of (iv) in a $C_1$–$C_3$ alcohol is treated sequentially with a solution of (iii)/(iiia), DME, and $K_2CO_3$ and stirred at reflux until completion.

The compounds and processes of the present invention will be better understood in connection with the following examples, which are intended as an illustration of a method by which the compounds of the invention may be prepared and not a limitation upon the scope of the invention.

EXAMPLE 1

2-methoxy-5-(1-methyl-4-(3,4,5-trimethoxyphenyl)-1H-imidazol-5-yl)phenylamine

EXAMPLE 1A 4-methylbenzenesulfinic acid

A vigorously stirred solution of 4-methylbenzenesulfinic acid, sodium salt (150 g, 0.84 mol) in water (500 mL) and TMBE (250 mL) was treated dropwise with concentrated HCl (75 mL). The resulting two layers were separated, and the aqueous layer was extracted with TMBE (100 mL). The combined extracts were dried ($Na_2SO_4$), filtered, and concentrated to near dryness. The resulting white solid was triturated with hexanes (350 mL), filtered, and dried under vacuum to provide 96 g of the desired product.

EXAMPLE 1B ((4-methylphenyl)sulfonyl)(3,4,5-trimethoxyphenyl) methylformamide A mixture of Example 1A (22.3 g, 0.15 mol), 3,4,5-trimethoxybenzaldehyde (35.32 g, 0.18 mol), and camphorsulfonic acid (3.48 g, 15 mmol) in formamide (40 mL) was stirred vigorously at 65° C. for 16 hours, cooled to room temperature, and filtered. The resulting solid was washed several times with methanol and dried to provide 13.4 g of the desired compound.

EXAMPLE 1C N-methylidyne((4-methylphenyl) sulfonyl)(3,4,5-trimethoxyphenyl)methanaminium A solution of the Example 1B (13.8 g, 36.3 mmol) in DME (200 mL) at −10° C. was treated with $POCl_3$ (10.3 ml, 110 mmol) and triethylamine (25.3 mL, 181.5 mmol) in DME (20 mL), stirred at −5° C. for 3 hours, poured into ice cold water (500 mL) and extracted with ethyl acetate (3×120 mL). The combined extracts were washed with 10% $NaHCO_3$ and brine, dried ($MgSO_4$), filtered, concentrated to 20% of their original volume, and filtered to provide 7.5 g of the desired compound. The mother liquor was concentrated, and the concentrate was purified by column chromatography on silica gel with 1:1 ethyl acetate/hexanes to provide additional desired product.

MS (ESI(+)) m/z 362 $(M+H)^+$ and 377 $(M+NH_4)^+$; $^1H$ NMR (300 MHz, $CDCl_3$) δ 7.65 (d, J=8.1 Hz, 2H), 7.33 (d, J=8.1 Hz, 2H), 6.49 (s, 2H,), 5.53 (s, 1H), 3.87 (s, 3H), 3.78 (s, 6H), 2.47 (s, 3H); Anal. calcd for $C_{18}H_{19}NO_5S$: C, 59.82; H, 5.30; N, 3.88. Found: C, 59.90; H, 5.37; N, 3.86.

EXAMPLE 1D

A solution of 4-methoxy-3-nitrobenzaldehyde (181 mg, 1 mmol) and 2.0M methylamine in methanol (5 mL, 10 mmol) in ethanol (15 mL) was treated with acetic acid (0.5 mL), warmed to reflux for 2 hours, cooled to room temperature, treated sequentially with DME (5 mL), Example 1C (490 mg, 1.5 mmol) and $K_2CO_3$ (552 mg, 4 mmol), warmed to reflux again for 5 hours, cooled, poured into ice cold water (500 mL) and extracted with ethyl acetate (3×50 mL). The combined extracts were washed with 10% $NaHCO_3$ and brine, dried ($MgSO_4$), filtered, and concentrated. The concentrate was purified by column chromatography on silica gel with ethyl acetate to provide 385 mg of the desired product.

MS (ESI(+)) m/z 400 $(M+H)^+$; $^1H$ NMR (300 MHz, $CDCl_3$) δ 7.89 (d, J=1.7 Hz, 1H), 7.62 (s, 1H), 7.52 (dd, J=8.8, 2 Hz, 1H), 7.21 (d, J=8.5 Hz, 1H), 6.72 (s, 2H), 4.02 (s, 3H), 3.82 (s, 3H), 3.69 (s, 6H), 3.54 (s, 3H).

EXAMPLE 1E 2-methoxy-5-(1-methyl-4-(3,4,5-trimethoxyphenyl)-1H-imidazol-5-yl)phenylamine A mixture of Example 1D (11.0 g, 27 mmol) and $SnCl_2.2H_2O$ (12.43 g, 55.0 mmol) in 12M HCl (100 mL) and ethanol (300 mL) was refluxed for 6 hours and concentrated. The concentrate was diluted with water (1L), neutralized with 50% NaOH, and extracted with ethyl acetate. The extract was washed with brine, dried (MgSO$_4$), filtered, and concentrated. The concentrate was recryststallized from acetonitrile to provide 6.8 g of the desired product.

MS (ESI(+)) m/z 370 (M+H)$^+$ and 392 (M+Na)$^+$; $^1$H NMR (300 MHz, Example 1E.2HCl, CD$_3$OD) δ 9.14 (s, 1H), 7.68–7.56 (m, 4H), 6.65 (s, 2H), 4.07 (s, 3H), 3.79 (s, 3H), 3.74 (s, 3H), 3.70 (s, 3H), 3.69 (s, 3); Anal. calcd for C$_{20}$H$_{23}$N$_3$O$_4$.0.74(CH$_3$)$_2$C(O): C, 64.72; H, 6.71; N, 10.19. Found: C, 64.52; H, 6.62; N, 10.29.

EXAMPLE 2

2-methoxy-5-(1-methyl-5-(3,4,5-trimethoxyphenyl)-1H-imidazol-4-yl)phenylamine

EXAMPLE 2A

[(4-methylphenyl)sulfonyl](3,4,5-trimethoxyphenyl)methylformamide

4-Methoxy-3-nitrobenzaldehyde was processed as described for 3,4,5-trimethoxybenzaldehyde in Example 1B to provide the desired product.

EXAMPLE 2B (4-methoxy-3-nitrophenyl)-N-methylidyne((4-methylphenyl)sulfonyl)methanaminium Example 2B was processed as described for Example 1B in Example 1C to provide the desired product.

MS (ESI(+)) m/z 364 (M+NH$_4$)$^+$; $^1$H NMR (300 MHz, CDCl$_3$) δ 7.71–7.62 (m, 4H), 7.40 (m, 2H), 7.15 (d, J=8.8 Hz, 1H), 5.57 (s, 1H), 4.02 (s, 3H), 2.49 (s, 3H).

EXAMPLE 2C 2,3-dimethoxy-5-(4-(4-methoxy-3-nitrophenyl)-1-methyl-1H-imidazol-5-yl)phenyl-methyl ether 3,4,5-Trimethoxybenzaldehyde and Example 2B were processed as described for 4-methoxy-3-nitrobenzaldehyde and Example 1C, respectively, in Example 1D to provide the desired product.

MS (ESI(+)) m/z 400 (M+H)$^+$; $^1$H NMR (300 MHz, CDCl$_3$) δ 8.05 (d, J=2 Hz, 1H), 7.72 (d, J=8.8 Hz, 1H), 7.61(d, J=1.1 Hz, 1H), 6.96 (d, J=8.8 Hz, 1H), 6.54 (s, 2H), 3.94 (s, 3H), 3.92 (s, 3H), 3.83 (s, 6H), 3.54 (s, 3H).

EXAMPLE 2D 2-methoxy-5-(1-methyl-5-(3,4,5-trimethoxyphenyl)-1H-imidazol-4-yl)aniline Example 2C was processed as described for Example 1D in Example 1E to provide the desired product.

MS (APCI(+)) m/z 370 (M+H)$^+$; $^1$H (300 MHz, Example 2D.2HCl, CD$_3$OD) δ 9.07 (s, 1H), 7.35 (dd, J=8.5, 1.9 Hz, 1H), 7.22–7.17 (m, 2H), 6.78 (s, 2H), 3.96 (s, 3H), 3.84 (s, 3H), 3.80 (s, 6H), 3.78 (s, 3H). Anal. calcd for C$_{20}$H$_{23}$N$_3$O$_4$.0.50H$_2$O: C, 63.48; H, 6.39; N, 11.10. Found: C, 63.55; H, 6.71; N, 11.10.

EXAMPLE 3

5-(3-fluoro-4-methoxyphenyl)-1-methyl-4-(3,4,5-trimethoxyphenyl)-1H-imidazole

Example 1C was processed as described Example 1D (substituting 3-fluoro-4 methoxybenzaldehyde for 4-methoxy-3-nitrobenzaldehyde) to provide the desired product.

MS (DCI/NH$_3$) m/z 373 (M+H)$^+$; $^1$H (300 MHz, CDCl$_3$) δ 7.55 (s, 1H), 7.06–7.15 (m, 3H), 6.76 (s, 2H), 3.95 (s, 3H), 3.67 (s, 6H), 3.49 (s,3H); Anal. calcd for C$_{20}$H$_{21}$N$_2$O$_4$.HCl.0.46H$_2$O: C, 57.59; H, 5.54; N, 6.72. Found: C, 63.55; H, 5.45; N, 6.62.

EXAMPLE 4

N,N-dimethyl-4-[1-methyl-4-(3,4,5-trimethoxyphenyl)-1H-imidazol-5-yl]aniline

Example 1C was processed as described Example 1D (substituting 4-(dimethylamino)benzaldehyde for 4-methoxy-3-nitrobenzaldehyde) to provide the desired product.

MS (DCI/NH$_3$) m/z 368 (M+H)$^+$; $^1$H (300 MHz, CDCl$_3$) δ 7.55 (s, 1H) 7.18–7.30 (m, 2H) 6.76–6.90 (m, 4H) 3.80 (s, 3H) 3.67 (s, 6H) 3.02 (s, 6H); Anal. calcd for C$_{21}$H$_{25}$N$_3$O$_4$.23CH$_3$C(O)CH$_2$CH$_3$: C, 67.91; H, 6.98; N, 10.84. Found: C, 67.91; H, 6.83; N, 10.86.

What is claimed is:

1. A compound selected from the group consisting of
   2-methoxy-5-(1-methyl-4-(3,4,5-trimethoxyphenyl)-1H-imidazol-5-yl)phenylamine,
   5-(3-fluoro-4-methoxyphenyl)-1-methyl-4-(3,4,5-trimethoxyphenyl)-1H-imidazole, and
   N,N-dimethyl-4-(1-methyl-4-(3,4,5-trimethoxyphenyl)-1H-imidazol-5-yl)aniline.

2. A method of inhibiting tubulin polymerization in a mammal in recognized need of such treatment comprising administering to the mammal a therapeutically effective amount of a compound of claim 1.

3. A method of treating cancer in a mammal in recognized need of such treatment comprising administering to the mammal a therapeutically effective amount of a compound of claim 1.

4. A pharmaceutical composition which comprises a therapeutically effective amount of a compound of claim 1 in combination with a pharmaceutically acceptable carrier.

* * * * *